United States Patent

Kerb et al.

[11] 4,061,661
[45] Dec. 6, 1977

[54] $\Delta^{9(11)}$-5α-20-KETO STEROIDS AND PROCESS FOR THEIR PRODUCTION

[75] Inventors: Ulrich Kerb; Rudolf Wiechert; Otto Engelfried, all of Berlin, Germany

[73] Assignee: Schering Aktiengesellschaft, Berlin and Bergkamen, Germany

[21] Appl. No.: 693,848

[22] Filed: June 8, 1976

[30] Foreign Application Priority Data

June 11, 1975 Germany .............................. 2526373

[51] Int. Cl.² ................................................ C07J 1/00
[52] U.S. Cl. ............................ 260/397.45; 260/397.4
[58] Field of Search ........................ 260/397.4, 397.45

[56] References Cited
FOREIGN PATENT DOCUMENTS 1,380,248    1/1975    United Kingdom ............ 260/397.45

OTHER PUBLICATIONS

Chem Abstracts – vol. 68 (1968) pars. 29.224x.

Primary Examiner—Elbert L. Roberts
Attorney, Agent, or Firm—Millen & White

[57] ABSTRACT

3α-Hydroxy and 3α-acyloxy- $\Delta^{9(11)}$-5α-20-ketopregnenes of the formula

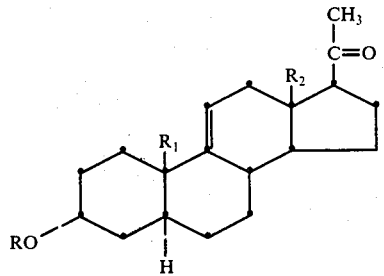

wherein R is hydrogen or acyl, $R_1$ is hydrogen or methyl and $R_2$ is methyl or ethyl, are produced by esterifying a corresponding 3β-hydroxy-5α-20-keto pregnane of the formula

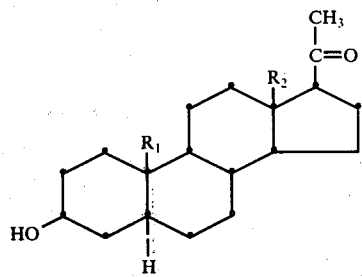

wherein $R_1$ and $R_2$ have the values given above, with m-iodobenzoic acid with inversion of the 3β-oxy group to a 3α-oxy group; chlorinating the thus-produced 3α-m-iodobenzoyl ester with dichloroiodobenzene under irradiation; and treating the reaction product with a dehydrohalogenating silver salt. Optionally thereafter, the 3α-iodobenzoyl group is split off in a conventional manner to produce the corresponding 3α-hydroxy steroid and optionally the thus-produced 3α-hydroxy steroid is esterified to produce a desired 3-ester thereof.

13 Claims, No Drawings

$\Delta^{9(11)}$-5α-20-KETO STEROIDS AND PROCESS FOR THEIR PRODUCTION

BACKGROUND OF THE INVENTION

This invention relates to a novel process for the production of 3α-hydroxy-$\Delta^{9(11)}$-5α-20-ketopregnenes and their esters.

It is known from the works by Breslow et al., e.g., J. Amer. Chem. Soc. 96 (1974) 1973; ibid. 96 (1974) 6791, that it is possible, in case of steroids esterified in the 3α-position, to chlorinate the tertiary $C_5$, $C_9$ and $C_{14}$ carbon atoms with dichloroiodobenzene under the influence of light and then split off hydrogen chloride again with the formation of a double bond at these positions.

However, this process has the disadvantage that it is applicable solely to those steroids which have no free carbonyl groups, such as 20-ketopregnanes.

In the process of this invention, 9α-chloro-20-ketopregnanes are selectively produced from which hydrogen chloride is subsequently split off with a silver salt in a conventional manner to form a $\Delta^{9(11)}$-double bond.

SUMMARY OF THE INVENTION

In a composition aspect, this invention relates to novel 3α-hydroxy- and 3α-acyloxy-$\Delta^{9(11)}$-5α-20-ketopregnenes of general Formula I

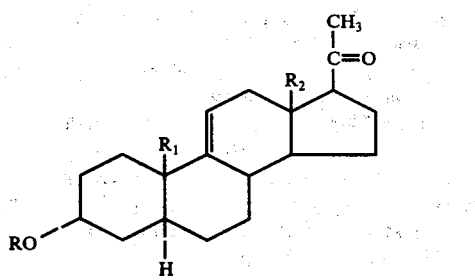

wherein R is hydrogen or acyl, $R_1$ is hydrogen or methyl and $R_2$ is methyl or ethyl.

In a process aspect, this invention relates to a process for their production comprising the steps of esterifying a 3β-hydroxy-5α-20-ketopregnane of general Formula II

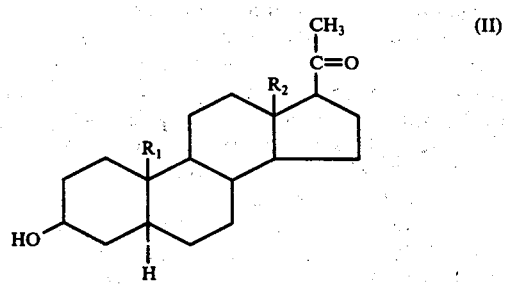

wherein $R_1$ and $R_2$ have the values given above, with the m-iodobenzoic acid with inversion of the 3α-oxy group to a 3α-oxy group; chlorinating the thus-produced 3α-m-iodobenzoyl ester with dichloroiodobenzene under irradiation; and treating the reaction product with a dehydrohalogenating silver salt. Optionally thereafter, the 3α-iodobenzoyl group is split off in a conventional manner to produce the corresponding 3α-hydroxy steroid and optionally the thus-produced 3α-hydroxy steroid is esterified to produce a desired 3-ester thereof.

DETAILED DISCUSSION

Examples of contemplated compounds embraced by Formula I are those wherein:

a. R is H;
b. R is $CH_3$;
c. $R_2$ is $CH_3$, including those of (a) and (b);
d. $R_2$ is $C_2H_5$, including those of each of (a) through (b);
e. $R_1$ is H, including those of each of (a) through (d);
f. $R_1$ is $CH_3$, including those of each of (a) through (d);
g. R is H, including those of each of (a) through (f);
h. R is m-iodobenzoyl, including those of each of (a) through (f); and
i. R is alkanoyl of 1–6 carbon atoms, including those of each of (a) through (f).

It is surprising that in the process of this invention chlorination occurs selectively at the 9-position, since U.S. Pat. No. 2,681,353 teaches that dichloroiodobenzene leads in the case of 20-ketopregnanes quantitatively to 21-chloro-20-ketopregnanes.

The process of this invention is a multistage process which is preferably conducted without isolating and/or working up the intermediate reaction products.

In the first reaction stage, the 3β-hydroxy group of the starting steroid of general Formula II is inverted in a conventional manner and desirably esterified at the same time.

The inversion of the 3β-hydroxy compounds to the 3α-form can be conducted in accordance with conventional isomerization methods. For example, 3α-hydroxy-19-nor-5α-pregnan-20-one can be produced from 3β-hydroxy-19-nor-5β-pregnan-20-one via their 3β-mesyloxy-, 3β-tosyloxy or other sulfonyloxy ester, which ester is then treated with a known inverting agent, e.g., lithium acetate under heating, and subsequently the 3-ester is hydrolyzed, e.g., with potassium hydroxide solution to regenerate the free 3-hydroxy group.

In a preferred embodiment, the 3β→3α-isomerization of the 3-hydroxy group is conducted with simultaneous esterification thereof, for example, 3β-hydroxy-5α-pregnan-20-one in a suitable solvent with a triaryl or trialkyl phosphine, e.g., triphenyl- or tributylphosphine, in the presence of the diethyl ester of azodicarboxylic acid and in the presence of the desired acid, such as, for example, m-iodobenzoic acid, to produce 3α-m-iodobenzoyl-5α-pregnan-20-one. Suitable solvents are all those inert relative to the reactants, e.g., tetrahydrofuran and dioxane. For a reference describing such inversion reaction, see Tetrahedron Letters, 1973, p. 1619.

In the second reaction stage, the thus-produced 3α-acyloxy-20-ketopregnane is photochemically halogenated with dichloroiodobenzene (phenyliodide dichloride) in a solvent. Suitable solvents are those which are not attacked by the halogenating agent employed, such as, for example, halogenated hydrocarbons, e.g., methylene chloride and chloroform, and aromatic hydrocarbons, e.g., benzene, chlorobenzene and toluene, and mixtures with one another. The introduction of an inert gas, such as, for example, nitrogen or argon, is advantageous during the reaction.

The photochemical reaction is induced by means of an ordinary sunlamp. For reference describing the type of irradiation which can be used, see, e.g., J. Amer. Chem. Soc. 96(1974)6791; ibid., 97(1975)6580.

In the third reaction stage, the thus-prepared 9α-halogen compound is treated in the homogeneous phase with a dehydrohalogenating silver salt, e.g., silver perchlorate, nitrate, acetate, or other silver salt soluble in the reaction solvent, whereupon the 9α-chlorine atom is split off as the insoluble silver chloride and is precipitated, with the formation of the $\Delta^{9(11)}$-double bond. Solvents which permit operation in an homogeneous phase are those in which the silver salt is soluble, such as, for example, acetone, acetic acid and water, and/or mixtures thereof. There is thus produced a compound of Formula I wherein R is acyl.

Optionally, a fourth reaction stage can follow the above-described states wherein the 3α-acyloxy group is split off in a conventional manner to produce a compound of Formula I wherein R is H. Especially suitable is alkaline saponification, e.g., employing a methanolic potassium hydroxide solution.

Optionally, a fifth reaction stage can follow, wherein the free 3α-hydroxy group is re-esterified in a conventional manner to form the desired final 3-ester group. A preferred method is the reaction with a reactive acid derivative in the presence of an alkaline reagent, such as, for example, the reaction with an acid chloride or acid anhydride in the presence of pyridine.

In addition to m-iodobenzoyl, in the compounds of Formula I, R can be the acyl radical of an alkanoic acid of up to 6 carbon atoms, e.g., acetyl, propionyl, butyryl and isobutyryl, as well as pivaloyl, formyl, pentanoyl, 2-methylbutyryl and hexanoyl. Contemplated equivalents of these alkanoyl esters are 3-esters of higher alkanoic acids, e.g., of 7-16 carbon atoms and other saturated, unsaturated, branched and polybasic carboxylic acids, including those substituted in the usual manner, for example, by hydroxy or halogen atoms; as well as of cycloaliphatic, mixed aromatic-aliphatic (alkaryl and aralkyl) acids, which can likewise be substituted in the usual manner. Examples of such contemplated equivalent esters are esters of triethylacetic, enanthic, octanoic, undecyclic, oleic and palmitic acid, cyclic acids, e.g., cycloaliphatic acids, containing, e.g., 5-18 carbon atoms, e.g., cyclopropylideneacetic, cyclobutylcarboxylic, cyclopentylcarboxylic, cyclopentylacetic, cyclohexylacetic, β-cyclopentylpropionic and β-cyclohexylpropionic acid, aroyl acids, e.g., mono or bicyclic aryl carbocyclic acid of 6–18 carbon atoms and 1 to 5, preferably 1 or 2 rings, e.g., benzoic o-, m- or p-methylbenzoic, o-, m- or p-fluorobenzoic, o-, m- or p-chlorobenzoic, α-naphthoic, β-naphthoic carbonyl, and other 2,3-, 2,4-, 2,5-, 2,6-, 3,4- and 3,5-dimethylbenzoic, ethylbenzoic, 2,3,6-trimethylbenzoic and 3-methyl-α-naphthoic acid; an aralkyl acid, e.g., containing 7 to 18 carbon atoms, e.g., phenylacetic, β-phenylpropionic, a polybasic acid, e.g., containing 2-18 carbon atoms and 1 to 5 hydroxy groups, e.g., glycolic, lactic, citric, tartaric, d-maleic, succinic, d-glyceric and salicyclic acid; and the corresponding acids containing one, two or more of simple substituents, e.g., halo, alkoxy, acyloxy, etc., in the molecule, e.g., chloroacetic, fluoroacetic, dichloroacetic, trichloroacetic, trifluoroacetic, 2,3,4-trimethoxybenzoic, phenoxyacetic and α-naphthoxyacetic acid. Also contemplated as equivalents are 3-esters of sulfonic, e.g., methanesulfonic and p-toluenesulfonic, and phosphoric acids.

The compounds of general Formula I which can be produced according to the process of this invention are useful intermediates for the preparation of pharmacologically valuable compounds. The thus-prepared compounds are 11β-hydroxy- and 11β-oxo-20-ketopregnanes having CNS-depressant activity. See German Offenlegungsschrift Nos. 2,065,513 and 2,255,108. They are prepared by reacting the compounds of Formula I with N-bromosuccinimide in an aqueous solution of dioxane to the halohydrin; heating the 9α-bromo-11β-hydroxypregnane dissolved in tetrahydrofuran with tributyltin hydride in the presence of azodiisobutyronitrile; oxidizing the 11β-hydroxy compound employing chromic acid in a suitable reaction medium, e.g., glacial acetic acid or sulfuric acid/acetone or pyridine/methylene chloride.

In our concurrently-filed application Ser. No. 693,847,—copending whose disclosure is incorporated herein by reference, we claim D-homo-pregnenes otherwise corresponding to the pregnenes of Formula I and the process for preparing them otherwise corresponding to the herein-claimed process.

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever.

PREPARATION

The 3β-hydroxy-18-methyl-19-nor-5α-pregnanes, which have not been described heretofore, can be obtained by reducing the corresponding 3-keto compounds, as illustrated below.

1.5 g. of 18-methyl-19-nor-5β-pregnane-3,20-dione is reduced in 18 ml. of pyridine with 0.15 g. of sodium borohydride for 24 hours at room temperature. After preparative layer chromatography, the crude product yields 0.86 g. of 3β-hydroxy-18-methyl-19-nor-5α-pregnan-20-one, m.p. 160°–161° C.

EXAMPLE 1

7.4 g. of 3β-hydroxy-5α-pregnan-20-one is dissolved in 140 ml. of tetrahydrofuran and 12.5 g. of triphenylphosphine and 8.2 g. of m-iodobenzoic acid are added to the reaction mixture. Under agitation, 7.1 ml. of the diethyl ester of azodicarboxylic acid is added dropwise thereto. The reaction solution is further stirred for 20 minutes and poured into 1 liter of ice water. The thus-precipitated product is filtered off, taken up in methylene chloride, washed with water, and evaporated under vacuum. The residue is chromatographed on silica gel, thus obtaining 13.5 g. of amorphous 3α-m-iodobenzoyloxy-5α-pregnan-20-one which melts at 150°–151.5° C. after recrystallization from pentane.

13.5 g. of 3α-m-iodobenzoyloxy-5α-pregnan-20-one is dissolved in 2400 ml. of methylene chloride. 8.4 g. of freshly prepared iodobenzene dichloride is introduced into the reaction mixture and the latter is irradiated with three 300-watt "Comptalux"*) lamps for 80 minutes while argon is introduced. Thereafter, the solution is concentrated under vacuum, dissolved in 1500 ml. of acetone, combined with a solution of 15.3 g. of silver perchlorate in 50 ml. of water, and agitated for 15 minutes. The thus-precipitated silver chloride is then removed by suction filtering, and the filtrate is concentrated under vacuum. The residue is taken up in ethyl acetate, washed with sodium chloride solution and water, dried over sodium sulfate, and evaporated. A sample of 3α-m-iodobenzoyloxy-5α-pregn-9(11)-en-20-one is recrystallized from methanol and melts at 136°–137° C.

*) internal mirror-coating sunlamp, Philips, Holland

The main quantity of the thus-obtained crude 3α-m-iodobenzoyloxy-5α-pregn-9(11)-en-20-one is heated under reflux for 3 hours in 500 ml. of methanol with 3 g. of potassium hydroxide. After neutralization with 4 ml. of glacial acetic acid, the solution is concentrated by evaporation, taken up in ethyl acetate, washed with water, dried over sodium sulfate, and evaporated. After chromatography and recrystallization from acetone-hexane, 4.7 g. of 3α-hydroxy-5α-pregn-9(11)-en-20-one is obtained, m.p. 169°–170° C.

EXAMPLE 2

790 mg. of 3α-m-iodobenzoyloxy-5α-pregn-9(11)-en-20-one is heated under reflux for 4 hours in 50 ml. of methanol with 200 mg. of potassium hydroxide. The mixture is then neutralized with acetic acid, evaporated, taken up in methylene chloride, and washed with sodium bicarbonate solution and water. A sample recrystallized from acetone melts at 168°–169° C. After removing the solvent under vacuum, the residue is stirred in 3 ml. of pyridine and 1.5 ml. of acetic anhydride for 16 hours at room temperature, poured into ice water, and the thus-precipitated produce is vacuum-filtered, dried, and recrystallized from methanol. Yield: 322 mg. of 3α-acetoxy-5α-pregn-9(11)-en-20-one, m.p. 158°–158.5° C.

EXAMPLE 3

Analogously to Example 1, the following compounds are prepared:

3.1  3α-Hydroxy-19-nor-5α-pregn-9(11)-en-20-one; m.p. 155°–156° C.,
from 3β-hydroxy-19-nor-5α-pregnan-20-one (prepared from 19-nor-5α-pregnane-3,20-dione according to U.S. Pat. No. 3,214,427 by reduction with sodium borohydride in pyridine; m.p. 147.5°–148° C.).

3.2  3α-Hydroxy-18-methyl-19-nor-5α-pregn-9(11)-en-20-one; m.p. 173°–175° C.,
from 3β-hydroxy-18-methyl-19-nor-5α-pregnan-20-one by way of 3α-iodobenzoyloxy-18-methyl-19-nor-5α-pregnan-20-one; m.p. 154°–155° C.

The preceding examples can be repeated with similar success by substituting the generically and specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A process for the production of a 3α-acyloxy-9α-chloro-5α-20-ketopregnane of the formula

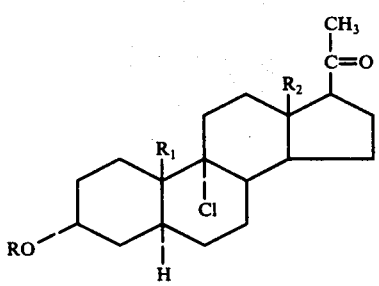

wherein R is the acyl radical of a carboxylic acid of up to 16 carbon atoms, $R_1$ is hydrogen or methyl and $R_2$ is methyl or ethyl, which comprises chlorinating a compound of the formula

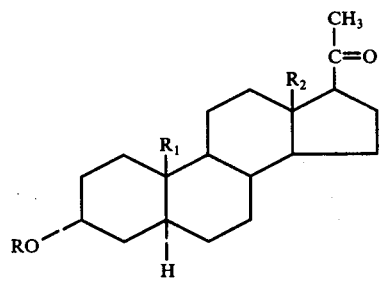

wherein R, $R_1$ and $R_2$ have the values given above, with iodobenzene dichloride under irradiation.

2. A process according to claim 1 wherein R is m-iodobenzoyl.

3. A process according to claim 2 wherein the starting compound is produced by esterifying a 3β-hydroxy-5α-20-ketopregnan of the formula

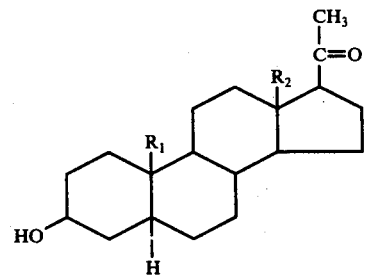

wherein $R_1$ and $R_2$ have the values given above, with m-iodobenzoic acid with inversion of the 3β-oxy group to a 3α-oxy group, by reaction with a triaryl or trialkyl phosphine in the presence of the diethyl ester of azodicarboxylic acid and the selected esterifying acid.

4. A process according to claim 1 comprising the further step of treating the thus-produced 9α-chloro steroid with a dehydrohalogenating silver salt to produce the corresponding 3α-acyloxy-Δ$^{9(11)}$-5α-20-ketopregnene.

5. A compound of formula

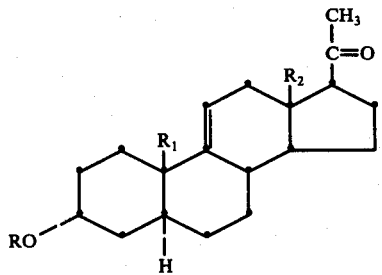

wherein n is 1 or 2, R is m-iodobenzoyl, $R_1$ is hydrogen or methyl and $R_2$ is methyl or ethyl.

6. A compound of claim 5 wherein $R_1$ is H.
7. A compound of claim 6 wherein $R_2$ is methyl.
8. A compound of claim 6 wherein $R_2$ is ethyl.
9. A compound of claim 5 wherein $R_1$ is methyl.
10. A compound of claim 9 wherein $R_2$ is methyl.
11. A compound of claim 9 wherein $R_2$ is ethyl.
12. A compound of claim 5, 3α-m-iodobenzoyloxy-5α-pregn-9(11)-en-20-one.
13.  3α-Iodobenzoyloxy-18-methyl-19-nor-5α-pregnan-20-one.

* * * * *